US010272243B2

(12) United States Patent
Nishimura et al.

(10) Patent No.: US 10,272,243 B2
(45) Date of Patent: Apr. 30, 2019

(54) CONTROL DEVICE FOR ELECTRICAL STIMULATION APPARATUS, ELECTRICAL STIMULATION APPARATUS, AND PEDALING EXERCISE SYSTEM

(71) Applicant: Panasonic Intellectual Property Management Co., Ltd., Osaka (JP)

(72) Inventors: Yoshinari Nishimura, Shiga (JP); Ryo Ichimura, Shiga (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 26 days.

(21) Appl. No.: 15/648,482

(22) Filed: Jul. 13, 2017

(65) Prior Publication Data

US 2018/0056061 A1 Mar. 1, 2018

(30) Foreign Application Priority Data

Aug. 30, 2016 (JP) .................................. 2016-168518

(51) Int. Cl.
*A61N 1/36* (2006.01)
*A61N 1/04* (2006.01)
(Continued)

(52) U.S. Cl.
CPC ......... *A61N 1/3603* (2017.08); *A61N 1/0452* (2013.01); *A61N 1/36003* (2013.01);
(Continued)

(58) Field of Classification Search
CPC .............. A61N 1/3603; A63B 22/0605; A63B 23/0476; A63B 2213/004; A63B 2220/34
See application file for complete search history.

(56) References Cited

U.S. PATENT DOCUMENTS 5,722,915 A * 3/1998 Reck ................ A63B 21/00178
482/1
7,381,192 B2 * 6/2008 Brodard ............... A61H 1/0255
601/33
(Continued)

FOREIGN PATENT DOCUMENTS

| JP | 2003-144556 | 5/2003 |
| JP | 2004-504921 A | 2/2004 |
| JP | 2016-086969 A | 5/2016 |

OTHER PUBLICATIONS

The Extended European Search Report dated Jan. 4, 2018 for the related European Patent Application No. 17183951.7.

*Primary Examiner* — Tammie K Marlen
(74) *Attorney, Agent, or Firm* — McDermott Will & Emery LLP

(57) ABSTRACT

A control device for an electrical stimulation apparatus according to the present disclosure includes a control section that adjusts an output of an electrode and communicates with an angular velocity detector, the electrode giving electrical stimulation to a predetermined part of a body doing a pedaling exercise by rotating a crank, the predetermined part being at least one of a leg and an arm, the angular velocity detector detecting an angular velocity of the predetermined part, the angular velocity being accompanied by an operation of the predetermined part during the pedaling exercise. The control section adjusts, according to a result of the detection in the angular velocity detector, an output timing of the electrical stimulation of the electrode such that the electrode gives electrical stimulation to the predetermined part when a state of the operation of the predetermined part during the pedaling exercise is a predetermined operation state.

8 Claims, 13 Drawing Sheets

(51) Int. Cl.
*A63B 22/06* (2006.01)
*A63B 23/04* (2006.01)

(52) U.S. Cl.
CPC ...... *A63B 22/0605* (2013.01); *A63B 23/0476* (2013.01); *A63B 2213/004* (2013.01); *A63B 2220/34* (2013.01)

(56) References Cited

U.S. PATENT DOCUMENTS

2004/0023759 A1* 2/2004 Duncan .............. A61N 1/36003
 482/57
2009/0018612 A1 1/2009 Duncan et al.

* cited by examiner

CONTROL DEVICE FOR ELECTRICAL STIMULATION APPARATUS, ELECTRICAL STIMULATION APPARATUS, AND PEDALING EXERCISE SYSTEM

BACKGROUND

1. Technical Field

The present disclosure relates to a control device for an electrical stimulation apparatus that electrically stimulates predetermined parts of a user's body while a user is doing pedaling exercise, to an electrical stimulation apparatus, and to a pedaling exercise system.

2. Description of the Related Art

Unexamined Japanese Patent Publication No. 2003-144556 discloses an electrical stimulation apparatus that helps a user do pedaling exercise or intensifies the pedaling exercise. More specifically, this electrical stimulation apparatus electrically stimulates the lower limbs, based on locations or rotation angles of the pedals.

SUMMARY

A relationship between a location or a rotation angle of a pedal and an angle of a knee joint of a lower limb may differ from a fundamentally desirable relationship due to various factors. This difference causes a concern that an electrical stimulation apparatus has difficulty in electrically stimulating the lower limb at an appropriate timing.

One embodiment of a control device for an electrical stimulation apparatus according to the present disclosure includes a control section that adjusts an output of an electrode and communicates with an angular velocity detector, the electrode giving electrical stimulation to a predetermined part of a body doing a pedaling exercise by rotating a crank, the predetermined part being at least one of a leg and an arm, the angular velocity detector detecting an angular velocity of the predetermined part, the angular velocity being accompanied by an operation of the predetermined part during the pedaling exercise. The control section adjusts, according to a result of the detection in the angular velocity detector, an output timing of the electrical stimulation of the electrode such that the electrode gives electrical stimulation to the predetermined part when a state of the operation of the predetermined part during the pedaling exercise is a predetermined operation state.

The control device for an electrical stimulation apparatus, the electrical stimulation apparatus, and the pedaling exercise system can electrically stimulate the predetermined part of a body doing pedaling exercise at an appropriate timing.

Figure 1:
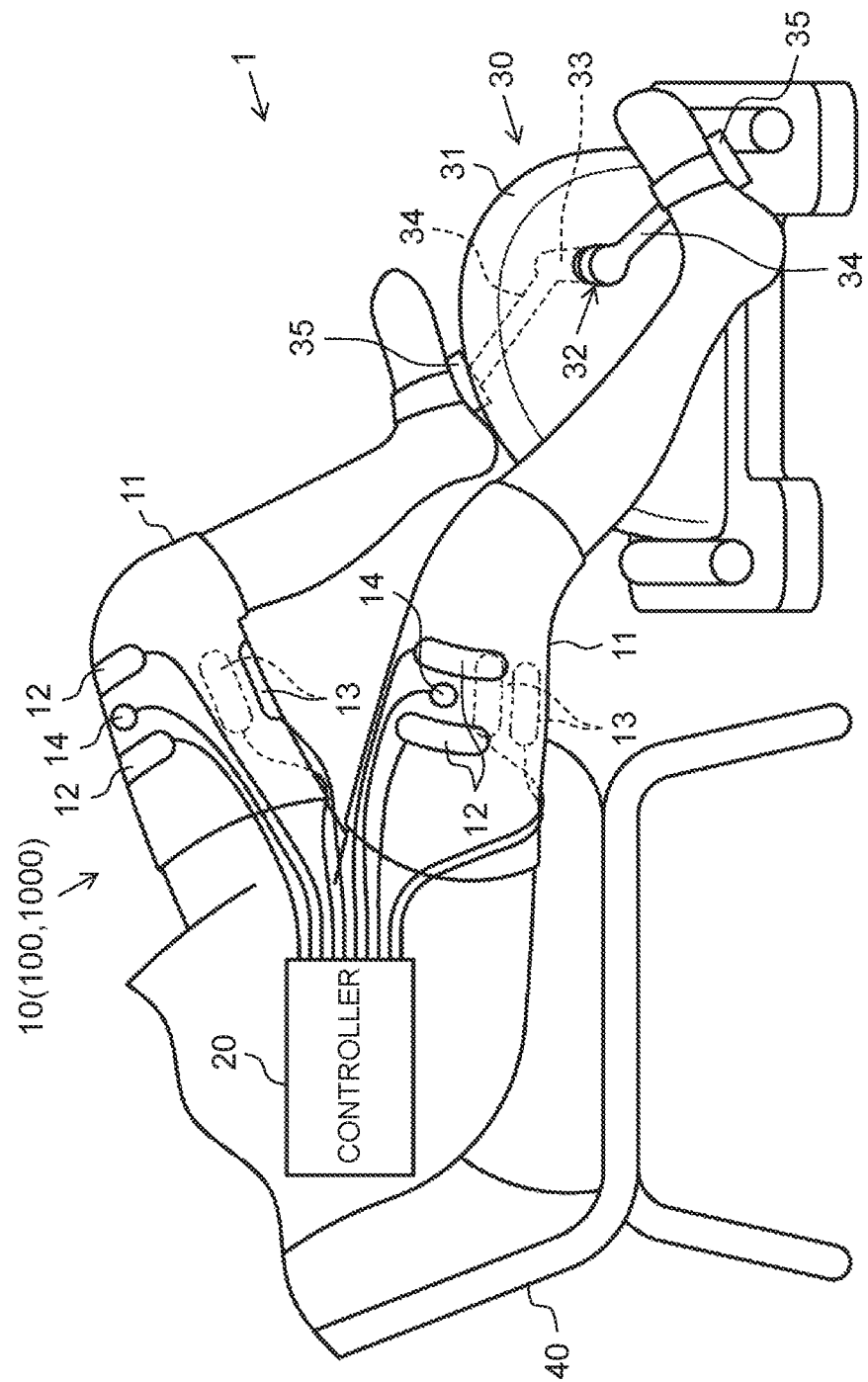
FIG. 1 is a perspective view of a pedaling exercise system according to an exemplary embodiment.

DETAILED DESCRIPTION (One Example of Embodiments of Control Device for Electrical Stimulation Apparatus, Electrical Stimulation Apparatus, and Pedaling Exercise System)

One embodiment of a control device for an electrical stimulation apparatus according to the present disclosure includes a control section that adjusts an output of an electrode and communicates with an angular velocity detector, the electrode giving electrical stimulation to a predetermined part of a body doing a pedaling exercise by rotating a crank, the predetermined part being at least one of a leg and an arm, the angular velocity detector detecting an angular velocity of the predetermined part, the angular velocity being accompanied by an operation of the predetermined part during the pedaling exercise. The control section adjusts, according to a result of the detection in the angular velocity detector, an output timing of the electrical stimulation of the electrode such that the electrode gives electrical stimulation to the predetermined part when a state of the operation of the predetermined part during the pedaling exercise is a predetermined operation state.

Consequently, the angular velocity detector can directly detect the operation state of the predetermined part of the body that does the pedaling exercise. Hence, when the angular velocity detector is attached to, for example, a lower limb, even if a relationship between a location or a rotation angle of a pedal and an angle of a knee joint of the lower limb differs from a fundamentally desirable relationship, it is possible to accurately detect the operation of the lower limb. Consequently, it is possible to electrically stimulate a predetermined part of a body that does the pedaling exercise at an appropriate timing during the pedaling exercise. In this regard, the predetermined operation state refers to a state defined as an operation state suitable for electrical stimulation.

According to one example of the control device for an electrical stimulation apparatus, the control section adjusts the output timing of a current of the electrode according to the result of the detection in the angular velocity detector and delay of the result of the detection in the angular velocity detector in response to the angular velocity of the predetermined part.

Consequently, even when the measured operation of the predetermined part delays from an actual operation of the predetermined part, it is possible to electrically stimulate the predetermined part at an appropriate timing for the actual operation of the predetermined part.

According to one example of the control device for an electrical stimulation apparatus, the control section adjusts the output timing based on a rotation speed of the crank.

By setting a timing of electrical stimulation that reflects an influence of a rotation speed of the crank due to delay of a detection result of the angular velocity detector with respect to the angular speed of the predetermined part, it is possible to electrically stimulate the predetermined part at an appropriate timing even when the rotation speed of the crank changes.

According to one example of the control device for an electrical stimulation apparatus, the control section smooths the result of the detection in the angular velocity detector by using a first filter when a number of revolutions of the crank during the pedaling exercise is included in a first range, and smooths the result of the detection in the angular velocity detector by using a second filter having a more moderate frequency response than the first filter when the number of revolutions of the crank during the pedaling exercise is included in a second range higher than the first range.

According to one example of the control device for an electrical stimulation apparatus, the control section detects, based on a representative value of a peak or a bottom of an angular velocity during a first period, a peak or a bottom of an angular velocity during a second period, the first period being a period in which the number of revolutions of the crank during the pedaling exercise is equal to or less than a predetermined number of revolutions, the second period being a period after the number of revolutions of the crank exceeds the predetermined number of revolutions.

Instead of using a value set in advance as a representative value, a peak or a bottom of the angular velocity of an individual user is measured at a start of the pedaling exercise to calculate the representative value. Consequently, it is possible to prevent timings of the peak or the bottom of the angular velocity from varying due to a physical size of the user. Consequently, it is possible to electrically stimulate the predetermined part of the individual user at an appropriate timing even when physical sizes of users vary.

According to one example of the control device for an electrical stimulation apparatus, the control section determines the output timing of the electrical stimulation based on a predetermined reference point. The control section determines the predetermined reference point based on a reference point determination condition set based on a variation of a plurality of items of angular velocity data acquired in advance. Consequently, it is possible to improve adjustment accuracy of the output timing for electrical stimulation.

According to one example of the control device for an electrical stimulation apparatus, the control section executes control to electrically stimulate the predetermined part at a timing during a first period, the timing being different from the output timing of the electrical stimulation adjusted by the control section, the first period being a period in which a number of revolutions of the crank during the pedaling exercise is equal to or less than a predetermined number of revolutions. Consequently, it is possible to reduce user discomfort.

According to one example of the control device for an electrical stimulation apparatus, the control section executes control not to electrically stimulate the predetermined part during a first period being a period in which a number of revolutions of the crank during the pedaling exercise is equal to or less than a predetermined number of revolutions.

The above electrical stimulation apparatus according to one embodiment includes: the above control device for an electrical stimulation apparatus, the electrode, and the angular velocity detector.

The above pedaling exercise system according to one embodiment includes the above electrical stimulation apparatus, and a pedaling exercise machine.

First Exemplary Embodiment

As illustrated in FIG. 1, pedaling exercise system 1 includes electrical stimulation apparatus 10, pedaling exercise machine 30, and a seat 40. Stimulation apparatus 10 is attached to user's lower limbs. The user does pedaling exercise using pedaling exercise machine 30 while sitting on seat 40. The configuration of pedaling exercise system 1 may be modified appropriately. As a first example, pedaling exercise machine 30 is integrated with seat 40. As a second example, pedaling exercise system 1 further includes a handle to be grabbed by the user's hand during the pedaling exercise. As a third example, seat 40 is provided with a mechanism that adjusts a height of seat 40. With this mechanism, the height of seat 40 can be adjusted so that the user does the pedaling exercise easily.

Electrical stimulation apparatus 10 electrically stimulates his/her lower limbs in accordance with the user's pedaling exercise. Electrical stimulation apparatus 10 includes supporters 11 and controller 20. Supporters 11 are attached to right and left lower limbs. Controller 20 is one example of a control device that controls electrical stimulation apparatus 10.

Each supporter 11 is provided with two first electrodes 12, two second electrodes 13, and angular velocity detector 14. First electrodes 12 and second electrodes 13 are disposed with a space being left therebetween. Two first electrodes 12 are disposed with a space being left therebetween. Two second electrodes 13 are disposed with a space being left therebetween. Angular velocity detector 14 is disposed closer to first electrodes 12 than second electrodes 13. More specifically, angular velocity detector 14 is disposed between two first electrodes 12, for example. In this case, each supporter 11 may have any number of first electrodes 12 and second electrodes 13. As one example, each supporter 11 may have one or not less than three first electrodes 12 and/or second electrodes 13.

When supporters 11 are attached to the lower limbs, first electrodes 12 are disposed at locations related to the quadriceps femorises of the lower limbs and second electrodes 13 are disposed at locations related to the biceps femorises of the lower limbs, for example. Angular velocity detectors 14 are disposed at locations related to the quadriceps femorises, for example. During the pedaling exercise, first electrodes 12 give electrical stimulation to the quadriceps femorises, second electrodes 13 give electrical stimulation to the biceps femorises, and angular velocity detectors 14 detect angular velocities of the quadriceps femorises. Angular velocity detectors 14 output detection signals according to the detected angular velocities to controller 20.

Controller 20 is electrically connected to supporters 11 by wires so as to be electrically connected to first electrodes 12, second electrodes 13, and angular velocity detectors 14. Controller 20 controls a mode of applying voltages to first electrodes 12 and second electrodes 13, based on detection signals from angular velocity detectors 14. Note that controller 20 may be wirelessly electrically connected to first electrodes 12, second electrodes 13, and angular velocity detectors 14.

Pedaling exercise machine 30 includes main body 31 and crank 32, for example. The main body 31 is installed on a floor, and crank 32 is provided with pedals 35. Main body 31 is provided with an electric motor (not illustrated) that rotates crank 32. Crank 32 includes crank shaft 33 and a pair of crank arms 34. Crank shaft 33 penetrates main body 31 with axial both ends protruding from main body 31. Crank arms 34 are connected to both ends of crank shaft 33 and extend perpendicularly to an axial direction of crank shaft 33. Pedals 35 are mounted to ends of crank arms 34.

Pedaling exercise machine 30 is provided with two operation modes including an automatic operation mode and a passive operation mode. In the automatic operation mode, crank 32 is rotated by the electric motor. In the passive operation mode, crank 32 is rotated by the pedaling exercise done by a user. During the passive operation mode, the electric motor stops, for example. Pedaling exercise machine 30 does not necessarily have to operate in the automatic operation mode. In this case, the electric motor is removed from pedaling exercise machine 30.

Figure 2:
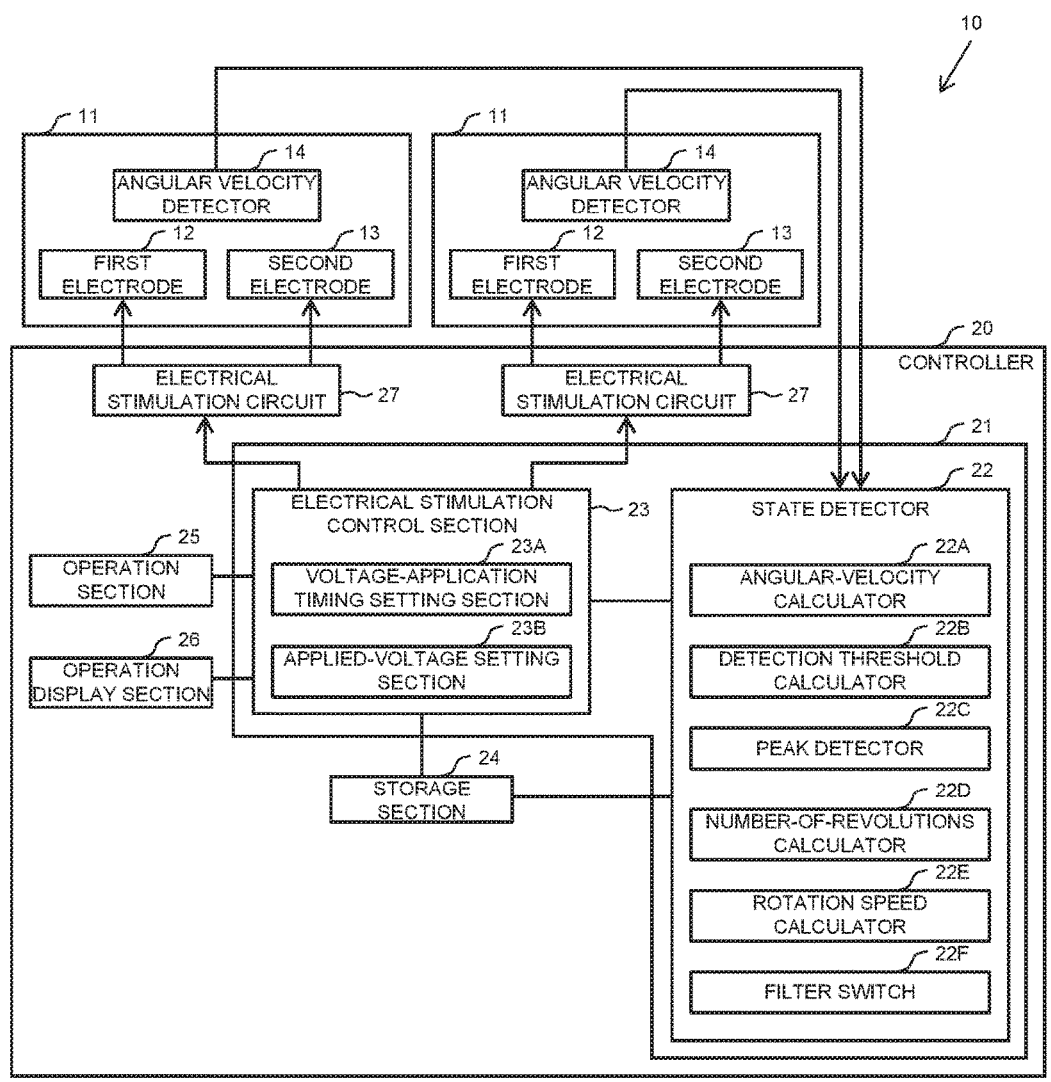
FIG. 2 is a block diagram of an electrical stimulation apparatus in the pedaling exercise system illustrated in FIG. 1.

With reference to FIG. 2, an electrical configuration of electrical stimulation apparatus 10 will be described.

Controller 20 includes control section 21, storage section 24, operation section 25, operation display section 26, and electrical stimulation circuits 27.

Control section 21 executes predetermined control programs. Control section 21 includes a central processing unit (a CPU) or a micro processing unit (an MPU). Control section 21 outputs control signals to electrical stimulation circuits 27 in order to control electrical stimulation circuits 27. Accordingly, control section 21 adjusts outputs from first electrodes 12 and second electrodes 13 that give electrical stimulation to lower limbs (legs) doing the pedaling exercise.

Storage section 24 stores information to be used for various control programs and control processes. Storage section 24 includes a random access memory (a RAM) and a read only memory (a ROM), for example. Storage section 24 may be incorporated into control section 21.

Operation section 25 allows a user to set voltages to be applied to first electrodes 12 and second electrodes 13 via electrical stimulation circuits 27, a period of the pedaling exercise during which the electrical stimulation is given, and an upper limit of a number of times that the electrical stimulation is given. Operation section 25 enables setting of voltages to be applied to first electrodes 12 and second electrodes 13 independently from each other. Hereinafter, the term "set voltage" refers to a voltage being strength of electrical stimulation set through operation section 25 among voltages applied to first and second electrodes 12, 13.

Operation display section 26 includes a liquid crystal panel, for example, and displays the contents set through operation section 25 and other information.

Electrical stimulation circuits 27 control the application of voltages to first electrodes 12 and second electrodes 13 in supporters 11, based on control signals from control section 21. Each electrical stimulation circuit 27 applies pulse voltages to first and second electrodes 12, 13. As a result, electric currents are output from first electrodes 12 and second electrodes 13.

Control section 21 includes state detector 22 and electrical stimulation control section 23. State detector 22 detects states of lower limbs, and a number of revolutions and a rotation speed of crank 32. Electrical stimulation control section 23 controls timings at which the voltages are applied to electrodes 12, 13 in supporters 11 and levels of the applied voltages.

State detector 22 includes angular-velocity calculator 22A, detection threshold calculator 22B, peak detector 22C, number-of-revolutions calculator 22D, rotation speed calculator 22E, and filter switch 22F. State detector 22 is electrically connected to electrical stimulation control section 23 and storage section 24.

Angular-velocity calculator 22A executes a filtering process on detection signals from each angular velocity detector 14 using a filter set by filter switch 22F so as to remove noise from the detection signals to smooth the detection signals. Angular-velocity calculator 22A calculates an angular velocity (referred below as "angular velocities AC") smoothed in such a manner. One example of this filtering process is a moving-average filtering process.

The detection threshold calculator 22B calculates a detection threshold which is used to detect a peak of angular velocity AC, based on angular velocity AC. For example, detection threshold calculator 22B acquires a peak of angular velocity AC for each rotation of crank 32 (see FIG. 1) within a first period. The first period is a period over which the number of revolutions of crank 32 is equal to or less than a predetermined number of revolutions RX. The peak of angular velocity AC is a maximum value of angular velocity AC within a range of transition from an increasing state to a decreasing state. Detection threshold calculator 22B then sets peak threshold XP, which is used to detect the peak of angular velocity AC, based on a plurality of peaks of angular velocity AC. In one example, detection threshold calculator 22B sets the average of the plurality of peak values to peak threshold XP.

Peak detector 22C compares angular velocity AC and peak threshold XP. Then, based on the comparison result, peak detector 22C detects a peak of angular velocity AC within a second period being a period that comes after the number of revolutions of crank 32 exceeds the predetermined number of revolutions RX.

Number-of-revolutions calculator 22D calculates the number of revolutions of crank 32, based on the number of peaks of angular velocity AC. Number-of-revolutions calculator 22D resets the number of revolutions of crank 32 which has been accumulated, when a rotation speed of crank 32 becomes zero.

Rotation speed calculator 22E calculates a rotation speed of crank 32, based on angular velocity AC.

A correlation holds between an angular velocity of a lower limb and a rotation speed of crank 32. Therefore, storage section 24 prestores information regarding the relationship between one cycle of angular velocity AC and a rotation speed of the crank 32, for example in a function or map format. Based on the information regarding the relationship between one cycle of angular velocity AC and a rotation speed of the crank 32, rotation speed calculator 22E calculates a rotation speed of crank 32 from the angular velocity calculated by angular-velocity calculator 22A. Note that, for example, rotation speed calculator 22E calculates one cycle of angular velocity AC, based on neighboring peaks of angular velocity AC.

Filter switch 22F includes a first filter and a second filter. A frequency response curve is steeper in the first filter than the second filter. The first filter provides a larger amount of reference data than the second filter. Each of the first and second filters is a low-pass filter. Note that each of the first and second filters may be a high-pass filter, a band-pass filter, or a resistor-capacitor (RC) filter.

Filter switch 22F switches between the first and second filters, based on the number of revolutions of crank 32. When the number of revolutions of crank 32 falls within a first range, filter switch 22F switches over to the first filter. When the number of revolutions of crank 32 falls within a second range that is wider than the first range, filter switch 22F switches over to the second filter. As one example, when the number of revolutions of crank 32 is equal to or less than the predetermined number of revolutions RX, filter switch 22F switches over to the first filter. When the number of revolutions of crank 32 exceeds the predetermined number of revolutions RX, filter switch 22F switches over to the second filter.

Immediately after a user starts doing the pedaling exercise, an exercise pace tends to be so unstable that noise is easily caused in a detection signal from each angular velocity detector 14. Therefore, when the number of revolutions of crank 32 is equal to or less than the predetermined number of revolutions RX, angular-velocity calculator 22A performs the filtering process using the first filter, thereby removing noise from the detection signal of angular velocity AC. Therefore, angular velocity AC is accurately calculated. After a considerable time has passed since a user has started doing the pedaling exercise, an exercise pace tends to be so stable that noise is hardly caused in a detection signal from each angular velocity detector 14. Therefore, when the number of revolutions of crank 32 exceeds the predetermined number of revolutions RX, angular-velocity calculator 22A performs the filtering process using the second filter. Performing this filtering process involves placing a lighter load on control section 21 than performing the filtering process using the first filter.

Electrical stimulation control section 23 includes voltage-application timing setting section 23A and applied-voltage setting section 23B.

Voltage-application timing setting section 23A adjusts output timings at which electrodes 12, 13 give electrical stimulation, in accordance with angular velocity AC. Adjusting the timings in this manner enables legs, which are predetermined parts of a body of a user doing the pedaling exercise, to be electrically stimulated when the legs are in a predetermined motion state. In one example, voltage-application timing setting section 23A applies a voltage to one of first and second electrodes 12, 13 which is related to the antagonistic muscles. In this case, a load is placed on the antagonistic muscles during the pedaling exercise.

Applied-voltage setting section 23B adjusts outputs of first electrodes 12 and second electrodes 13 so that the legs, which are predetermined parts of the body of the user doing the pedaling exercise, are electrically stimulated in relation to an exercise unit of the pedaling exercise. Applied-voltage setting section 23B adjusts strength of electrical stimulation related to an exercise unit, in accordance with the amount of a physical activity during the pedaling exercise. One example of the amount of a physical activity is the number of revolutions of crank 32. One example of an exercise unit is one revolution of crank 32. One example of strength of electrical stimulation is magnitude of an applied voltage.

Thus, applied-voltage setting section 23B sets voltages applied to respective electrodes 12, 13, based on the number of revolutions of crank 32. An applied voltage is set such that its magnitude gradually increases toward the set voltage, in accordance with increase in the number of revolutions of crank 32. Note that the exercise unit may be a plurality of revolutions of crank 32 or a predetermined time of the pedaling exercise.

With reference t to FIGS. 1 and 2, the usage of pedaling exercise system 1 will be described.

A user sits on seat 40 and then starts doing the pedaling exercise with pedaling exercise machine 30. In this case, the user preferably does the pedaling exercise so that crank 32 rotates within a recommended rotation speed range of crank 32 (for example, a range between 30 rpm and 60 rpm per minute, both inclusive). When the number of revolutions of crank 32 is equal to or less than the predetermined number of revolutions RX, electrical stimulation apparatus 10 does not apply a voltage to respective electrodes 12, 13. After the number of revolutions of crank 32 exceeds the predetermined number of revolutions RX, electrical stimulation apparatus 10 applies predetermined patterns of voltages to respective electrodes 12, 13 at predetermined timings.

Figure 4:
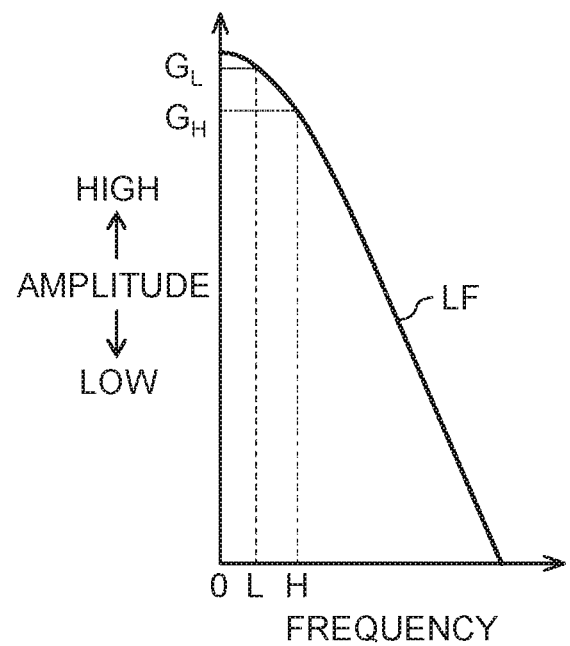
FIG. 4 is a graph illustrating a frequency response in the filtering process to be performed by the control section.
Figure 5:
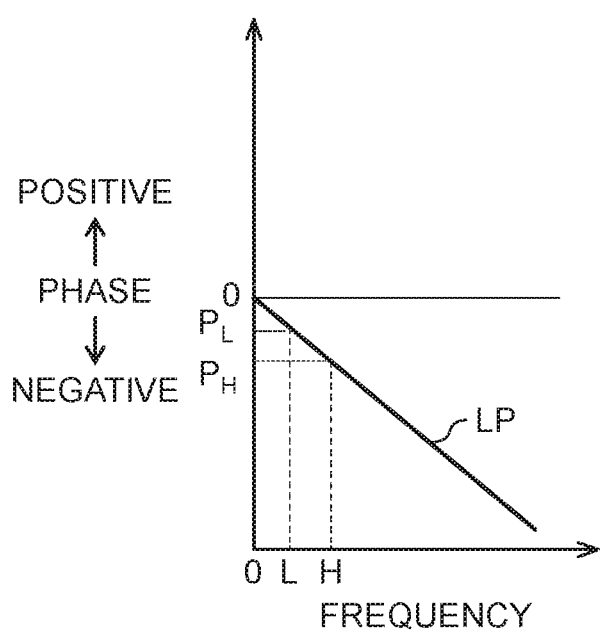
FIG. 5 is a graph illustrating a phase characteristic in the filtering process to be performed by the control section.
Figure 6:
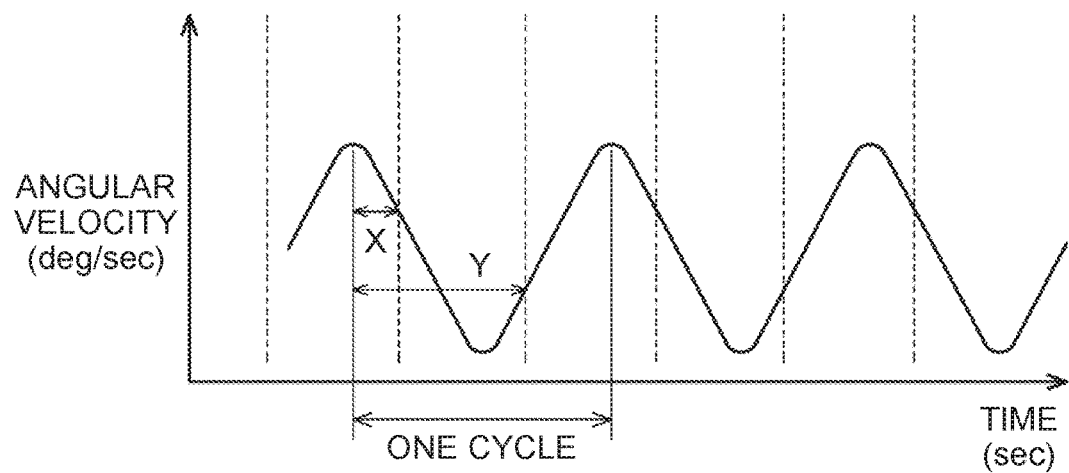
FIG. 6 is a graph illustrating one example of an angular velocity acquired after the filtering process when the crank rotates at a low speed.
Figure 7:
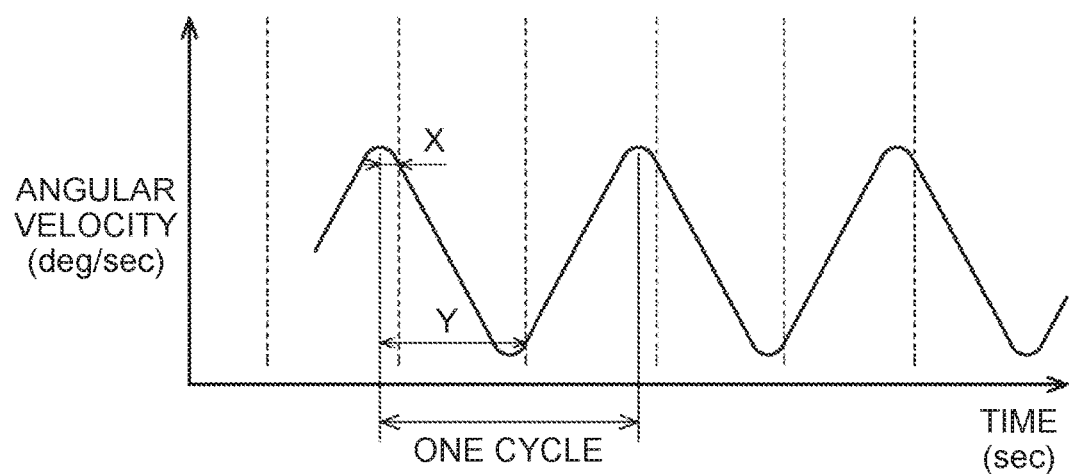
FIG. 7 is a graph illustrating one example of an angular velocity acquired after the filtering process when the crank rotates at a high speed.

With reference to FIGS. 3 to 7, a method for setting timings of applying voltages to respective electrodes 12, 13 will be described. In FIGS. 6 and 7, lengths of one cycle are equal to each other between angular velocity AC acquired when crank 32 rotates at a high speed and angular velocity AC acquired when crank 32 rotates at a low speed, for the purpose of easy understanding in relation to a difference in a phase delay amount of angular velocities AC.

Figure 3:
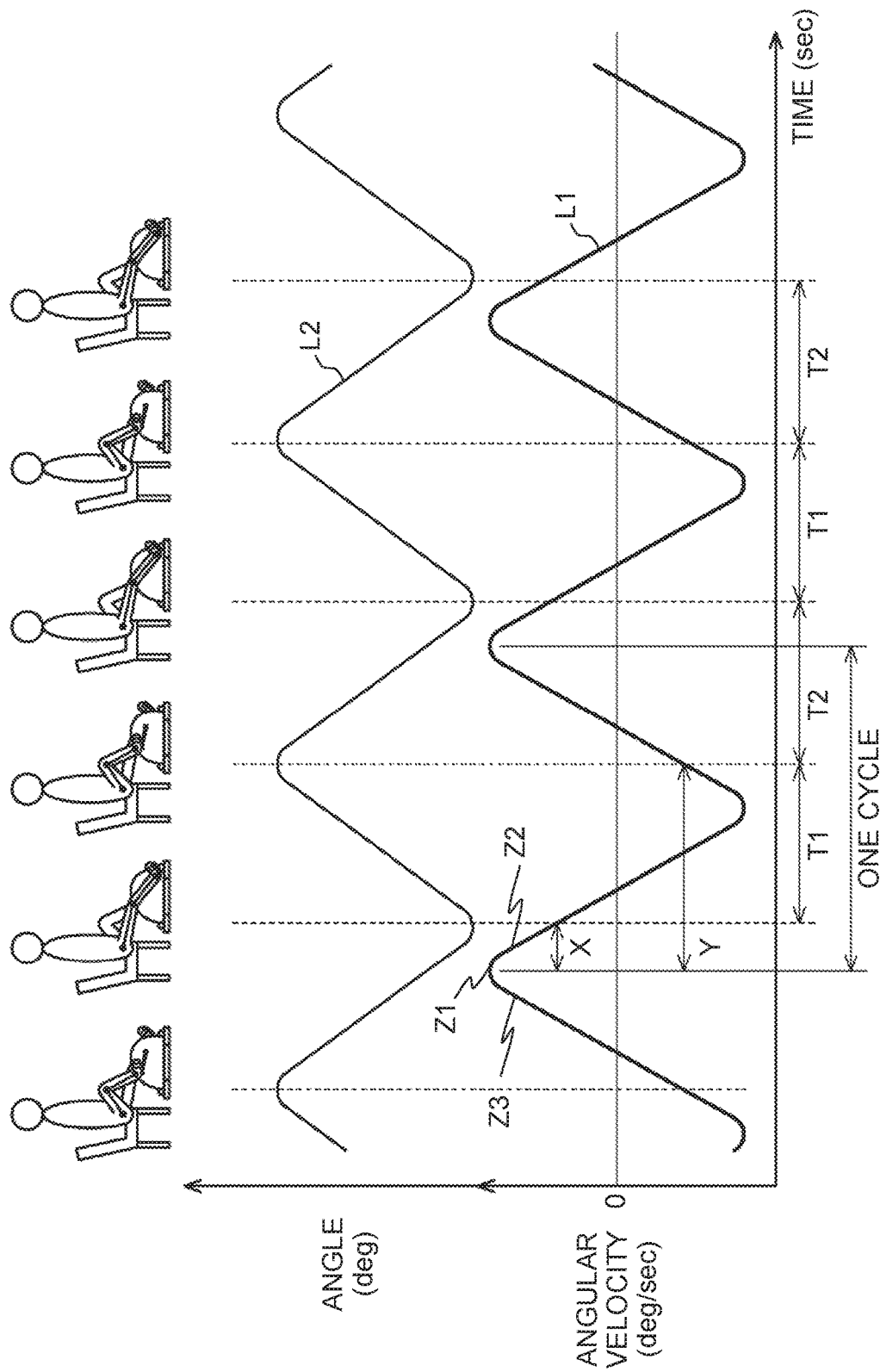
FIG. 3 is a graph illustrating changes in an angle of a knee joint and an angular velocity acquired after a filtering process.

In a graph of FIG. 3, upper line L2 represents a change in an angle of a right knee joint of a user while the user is doing the pedaling exercise. In the graph of FIG. 3, lower line L1 represents a change in an angular velocity detected by angular velocity detector 14 in supporter 11. The angular velocity represented by line L1 corresponds to angular velocity AC acquired as a result of the filtering process.

As can be understood from lines L1, L2, a phase difference between the angle of the right knee joint and angular velocity AC. More specifically, the phase of angular velocity AC is delayed from the phase of the angle of the right knee joint. The main cause of this phase delay of angular velocity AC is the filtering process.

In some cases, for example, wobbling of the crank and wobbling of the pedals with respect to the crank arm may cause noise to be superimposed on angular velocities detected by angular velocity detectors 14. Further, when a distance between seat 40 and pedaling exercise machine 30 differs from a recommended distance, noise may be overlapped on angular velocities detected by angular velocity detectors 14. The recommended distance is set so that the user can do the pedaling exercise easily. For these reasons, when calculating angular velocity AC, electrical stimulation apparatus 10 removes noise from an angular velocity detected by each angular velocity detector 14 using the first and second filters to smooth the angular velocity. Solid line LF drawn on a graph in FIG. 4 shows one example of a frequency response of the second filter. Solid line LP drawn on a graph in FIG. 5 shows one example of a phase characteristic of the second filter.

When angular velocity AC is calculated by the filtering process, the frequency response (phase characteristic) of the filter influences more strongly a phase delay of angular velocity AC with respect to an angle of the right knee joint as the rotation speed of crank 32 becomes higher. In FIG. 4, for example, at frequency $G_L$, line LF indicates a decrease in the amplitude of angular velocity AC with respect to the angular velocity detected by each angular velocity detector 14 when crank 32 rotates at a low speed. In FIG. 5, at frequency $P_L$, line LP indicates a phase delay of angular velocity AC with respect to the angular velocity detected by each angular velocity detector 14 when crank 32 rotates at a low speed. In FIG. 4, likewise, at frequency $G_H$, line LF indicates a decrease in the amplitude of angular velocity AC with respect to the angular velocity detected by each angular velocity detector 14 when crank 32 rotates at a high speed. In FIG. 5, at frequency $P_H$, line LP indicates a phase delay of angular velocity AC with respect to the angular velocity detected by each angular velocity detector 14 when crank 32 rotates at a high speed. As illustrated in FIG. 5, the phase delay of the second filter increases with an increase in a frequency. This causes the phase delay of angular velocity AC to increase with an increase in a rotation speed of crank 32. As a result, as shown on graphs regarding temporal transition of angular velocity AC in FIGS. 6 and 7, the phase delay of angular velocity AC is smaller when crank 32 rotates at a low speed than when crank 32 rotates at a high speed. As can be understood from FIGS. 6 and 7, ratio X for a high-speed rotation of crank 32 is lower than ratio X for a low-speed rotation of crank 32, and ratio Y for a high-speed rotation of crank 32 is lower than ratio Y for a low-speed rotation of crank 32. Details of the ratios X and Y will be described later.

Therefore, voltage-application timing setting section 23A sets timings at which voltages are applied to respective electrodes 12, 13 in accordance with a degree of the phase delay of angular velocity AC caused by the filtering process and a degree of the phase delay of angular velocity AC due to the rotation speed of crank 32. More specifically, the relationship between an angular velocity of a lower limb and an angle of a knee joint is predetermined and is prestored in storage section 24. Voltage-application timing setting section 23A sets timings at which voltages are applied to respective electrodes 12, 13, based on the relationship between an angular velocity of a lower limb and an angle of a knee joint.

By simultaneously measuring an angular velocity of a lower limb and an angle of a knee joint, a phase difference between the angle of the knee joint and angular velocity AC can be acquired. Then, by simultaneously measuring angular velocities of lower limbs and angles of the knee joints at various rotation speeds of crank 32, a degree of the phase difference between angular velocity AC and the angle of the knee joint due to a rotation speed of crank 32 can be acquired. In the graph of FIG. 3, line L1 represents one example of a measurement result of an angle of a knee joint, and line L2 represents one example of a measurement result of an angular velocity of a lower limb. Line L2 has a peak (a maximum value) when the knee joint is bent maximally, and has a bottom (a minimum value) when the knee joint stretches maximally.

Storage section 24 stores the phase differences between lines L1 and L2 at the peak and bottom of line L2, as the relationships between an angle of a knee joint and an angular velocity of a lower limb. Further, the phase difference between lines L1 and L2 at the bottom of line L2 is stored as a ratio (referred to below as a "ratio X") of a first phase difference related to one cycle of angular velocity AC. In the present exemplary embodiment, the phase difference between the peak of line L1 and the bottom of line L2 is stored as a ratio X of a first phase difference related to one cycle of angular velocity AC. The phase difference between lines L1 and L2 at the peak of line L2 is stored as a ratio Y (referred to below as a "ratio Y") of a second phase difference related to one cycle of angular velocity AC. In the present exemplary embodiment, the phase difference between the peak of line L1 and the peak of line L2 is stored as ratio Y of a second phase difference related to one cycle of angular velocity AC.

Figure 8:
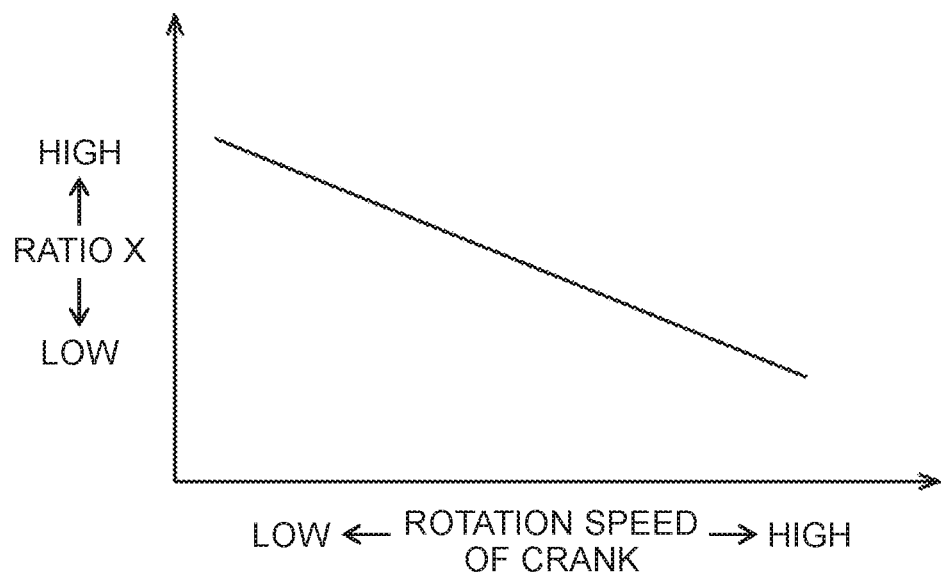
FIG. 8 is a graph illustrating a map for calculation of a timing of voltage application to a first electrode.
Figure 9:
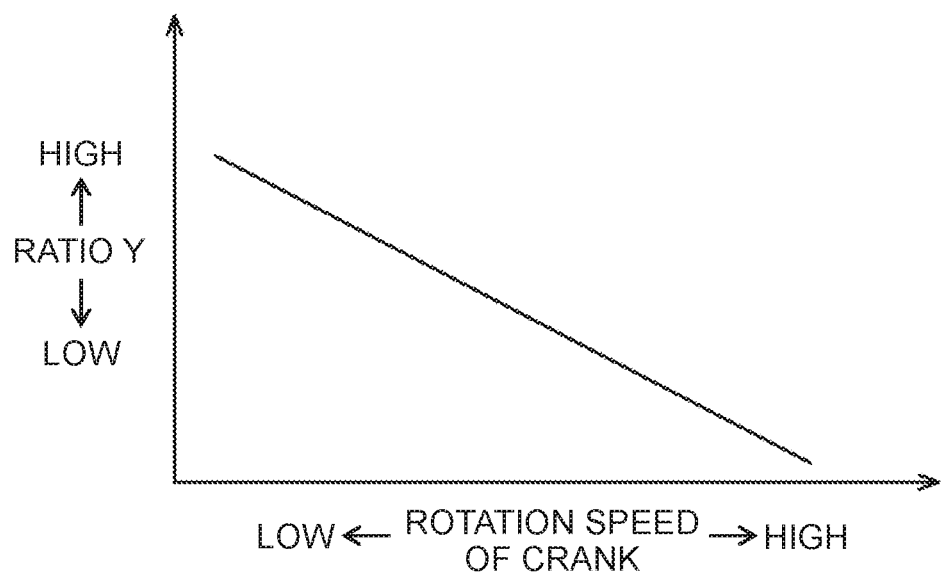
FIG. 9 is a graph illustrating a map for calculation of a timing of voltage application to a second electrode.

These ratios X, Y are stored in relation to various rotation speeds of crank 32. In one example, storage section 24 stores map MPX and map MPY. Ratio X is related to the rotation speed of crank 32 in map MPX as illustrated in FIG. 8. The ratio Y is related to the rotation speed of crank 32 in map MPY as illustrated in FIG. 9. In one example, in map MPX, ratio X decreases with an increase in the rotation speed of crank 32. In map MPY, ratio Y decreases with an increase in the rotation speed of crank 32.

Note that control section 21 may calculate ratios X, Y, based on a compensation equation, instead of based on map MPX of FIG. 8 and map MPY of FIG. 9. Ratio X can be defined as the compensation equation: $X = A1 \times R + B1$, where R denotes a rotation speed, A1 denotes gradient of the straight line in map MPX of FIG. 8, and B1 denotes an intercept of the straight line. Ratio Y can be defined as the compensation equation: $Y = A2 \times R + B2$, where A2 denotes gradient of the straight line in map MPY of FIG. 9, and B2 denotes intercept of the straight line.

Voltage-application timing setting section 23A sets a timing at which a voltage is applied to first electrodes 12, based on map MPX of FIG. 8 and a current rotation speed of crank 32. Likewise, voltage-application timing setting section 23A sets a timing at which a voltage is applied to second electrodes 13, based on map MPY of FIG. 9 and a current rotation speed of crank 32. As a result, when a lower limb stretches maximally during the pedaling exercise, voltage-application timing setting section 23A starts applying a voltage to the corresponding first electrodes 12 but stops applying a voltage to the corresponding second electrodes 13. When a lower limb is bent maximally during the pedaling exercise, voltage-application timing setting section 23A starts applying a voltage to the corresponding second electrodes 13 but stops applying a voltage to the corresponding first electrodes 12. In this way, electrical stimulation apparatus 10 can electrically stimulate quadriceps and biceps femorises at appropriate timings during the pedaling exercise. Furthermore, electrical stimulation apparatus 10 sets ratios X, Y in accordance with a rotation speed of crank 32. This can electrically stimulate quadriceps and biceps femorises at appropriate timings, in accordance with the pedaling exercise.

Further, over every first voltage-application period T1 (see FIG. 3), voltage-application timing setting section 23A applies a voltage to first electrodes 12 but does not apply a voltage to second electrodes 13. Over every second voltage-application period T2 (see FIG. 3), voltage-application timing setting section 23A applies a voltage to second electrodes 13 but does not apply a voltage to first electrodes 12. As illustrated in FIG. 3, first voltage-application period T1 corresponds to a time length between the application of the voltage to first electrodes 12 and the application of the voltage to second electrodes 13. Second voltage-application period T2 corresponds to time length between the application of the voltage to second electrodes 13 and the application of the voltage to first electrodes 12. Applying voltages in first application period T1 and second application period T2 in this manner enables a quadriceps femoris and biceps femoris to be electrically stimulated over the respective periods in which the quadriceps femoris and the biceps femoris stretch respectively.

A method for setting voltages applied to first and second electrodes 12, 13 will be described.

Storage section 24 stores information regarding the relationship between the number of revolutions of crank 32 and the voltages applied to respective electrodes 12, 13. When the number of revolutions of crank 32 is equal to or less than the predetermined number of revolutions RX, no voltages are applied to first and second electrodes 12, 13. According to this information, when the number of revolutions of crank 32 exceeds the predetermined number of revolutions RX, voltages are applied to first and second electrodes 12, 13. When the number of revolutions of crank 32 becomes RX+1, an initial voltage lower than the set voltage is applied to first and second electrodes 12, 13. Then, as the number of revolutions of crank 32 increases, the applied voltage gradually increases toward the set voltage. In this way, a load on each leg gradually increases during the pedaling exercise, at the start of the rotation of pedals 35. This suppresses the quadriceps and biceps femorises from bearing heavy loads suddenly. Consequently, user discomfort due to an increase in the load of the pedaling exercise can be suppressed.

Figure 10:
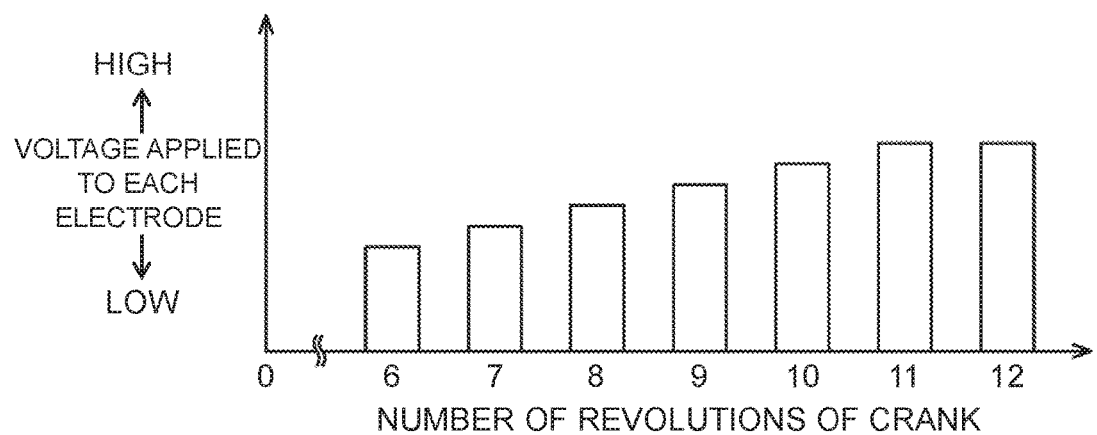
FIG. 10 is a graph illustrating a relationship between a number of revolutions of the crank and an applied voltage.

FIG. 10 illustrates one example of the above information. As can be understood from FIG. 10, when the number of revolutions of crank 32 is equal to or less than five, no voltages are applied to respective electrodes 12, 13. When the number of revolutions of crank 32 exceeds six, a voltage is applied to respective electrodes 12, 13. Further, when the number of revolutions of crank 32 is six, a voltage lower than the set voltage is applied to respective electrodes 12, 13. In the voltage application pattern in FIG. 10, the initial voltage applied when the number of revolutions of crank 32 is six is about 50% of the set voltage. When the number of revolutions of crank 32 falls within a range between seven and eleven, every time the number of revolutions of crank 32 increases by one, the voltage applied to respective electrodes 12, 13 increases by about 10%.

Figure 11:
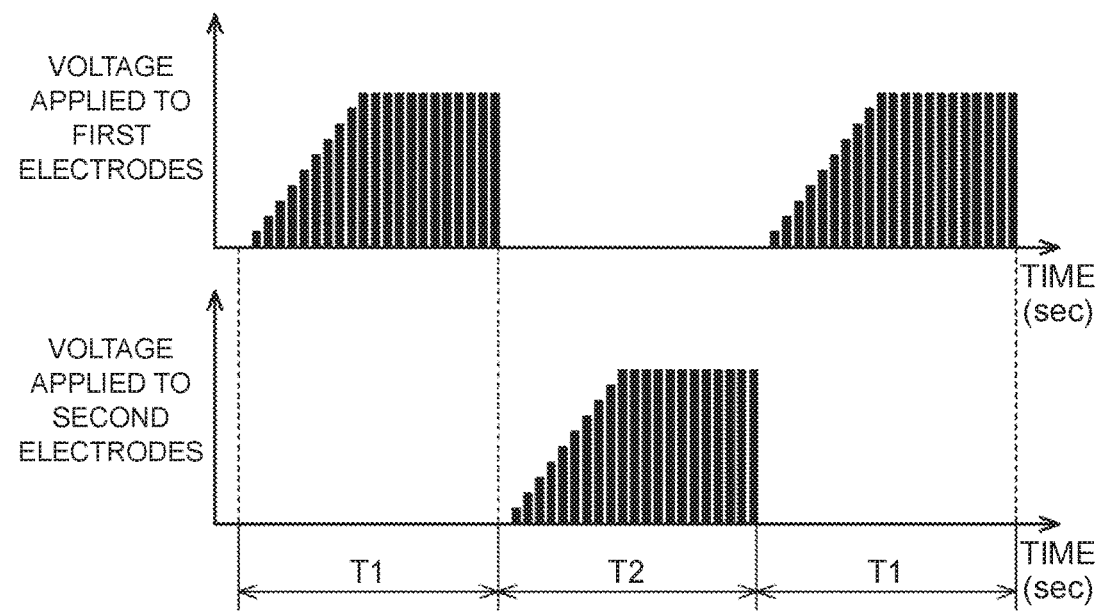
FIG. 11 is a graph illustrating the voltages applied to the respective electrodes.

Storage section 24 prestores magnitude of the voltage applied to first electrodes 12 over first voltage-application period T1 and magnitude of the voltage applied to second electrodes 13 over second voltage-application period T2. FIG. 11 illustrates an example of these applied voltage values. As can be understood from FIG. 11, voltages applied to respective electrodes 12, 13 gradually increase during first half parts including start points of voltage-application periods T1, T2. Then, after the first half parts of voltage-application periods T1, T2 have passed, the voltages applied to respective electrodes 12, 13 are kept constant. Upper limit values of the voltages applied to electrodes 12, 13 over voltage-application periods T1, T2 are upper limit values of voltages illustrated in FIG. 10. Operation section 25 can change increasing rates of the voltages applied to respective electrodes 12, 13 according to an increase in the number of revolutions of crank 32, and increasing rates of the voltage applied to electrodes 12, 13 over voltage-application periods T1, T2.

Applied-voltage setting section 23B sets the voltages applied to respective electrodes 12, 13 at each number of revolutions of crank 32 using the voltage-application pattern in FIG. 10. In addition, applied-voltage setting section 23B sets voltages applied to electrodes 12, 13 over first voltage-application period T1 and second voltage-application period T2 using the voltage-application patterns in FIG. 11.

In this way, the voltages applied to respective electrodes 12, 13 are set low at the beginning of respective voltage-application periods T1, T2. Then, the voltages gradually increase with time. This further suppresses the quadriceps and biceps femorises from bearing heavy loads suddenly. Consequently, user discomfort due to an increase in the load can be further suppressed.

In this case, first voltage-application period T1 and second voltage-application period T2 are shorter when crank 32 rotates at a high speed than when crank 32 rotates at a low speed. However, the voltages applied to first electrodes 12 and second electrodes 13 have constant frequencies. Therefore, after the number of revolutions of crank 32 exceeds eleven, ratios in which the set voltage is applied to respective electrodes 12, 13 are lower when crank 32 rotates at a high speed than when crank 32 rotates at a low speed. In this case, the ratio in which the voltage applied to first electrodes 12 is expressed by the equation: (a time when the set voltage is applied to first electrodes 12 during every first voltage-application period T1)/(first voltage-application period T1)×100. The ratio in which the voltage is applied to second electrodes 13 is expressed by the equation: (a time when the set voltage is applied to second electrodes 13 during second voltage-application period T2)/(second voltage-application period T2)×100.

Figure 12:
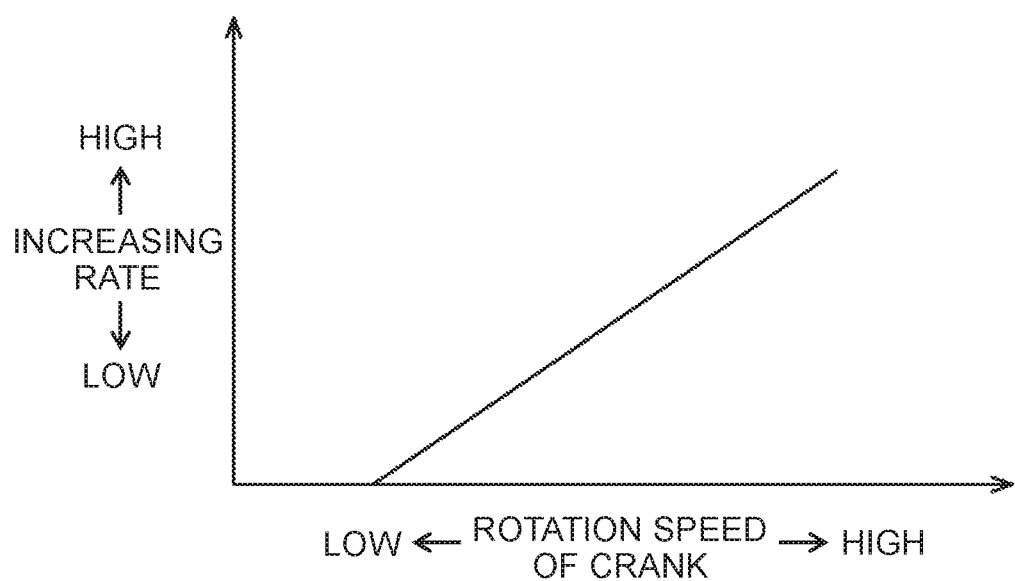
FIG. 12 is a graph illustrating a map illustrating a relationship between a rotation speed of the crank and an increasing rate of an applied voltage.

Therefore, applied-voltage setting section 23B adjusts increasing rates of the voltages applied to respective electrodes 12, 13 during voltage-application periods T1, T2 in accordance with the rotation speed of crank 32. More specifically, applied-voltage setting section 23B increases the increasing rates of the voltages applied to respective electrodes 12, 13 with an increase in the rotation speed of crank 32. Storage section 24 stores information regarding the relationship between the rotation speed of crank 32 and the increasing rates of the voltages applied to respective second electrodes 12, 13. This information may be stored in storage section 24 in a map format as illustrated in FIG. 12 or in a function format. In this exemplary embodiment, the increasing rate of the voltage applied to first electrodes 12 over first voltage-application period T1 is equal to the increasing rate of the voltage applied to second electrodes 13 over second voltage-application period T2. Thus, a single common map illustrated in FIG. 12 is used in the relationship between the rotation speed of crank 32 and the increasing rates of the voltages applied to respective electrodes 12, 13. Applied-voltage setting section 23B sets, using the map, for example as illustrated in FIG. 12, the increasing rates of the voltages applied to respective electrodes 12, 13 in accordance with the rotation speed of crank 32. This setting can reduce or reduce to zero the difference in ratio between the set voltage applied to respective electrodes 12, 13 when crank 32 rotates at a high speed and when crank 32 rotates at a low speed.

Various processes performed by control section 21 will be described below with reference to FIGS. 13 to 15.

Control section 21 performs a first process, a second process, and a third process. In the first process, control section 21 detects peaks of angular velocity AC within the period between a time when the pedaling exercise is started by a user and when the number of revolutions of crank 32 becomes the predetermined number of revolutions RX. In the second process that follows the first process, control section 21 sets timings at which voltages are applied to respective electrodes 12, 13. In the third process that follows the first process, control section 21 sets magnitude of voltages applied to respective electrodes 12, 13. The second process and the third process are simultaneously performed.

Figure 13:
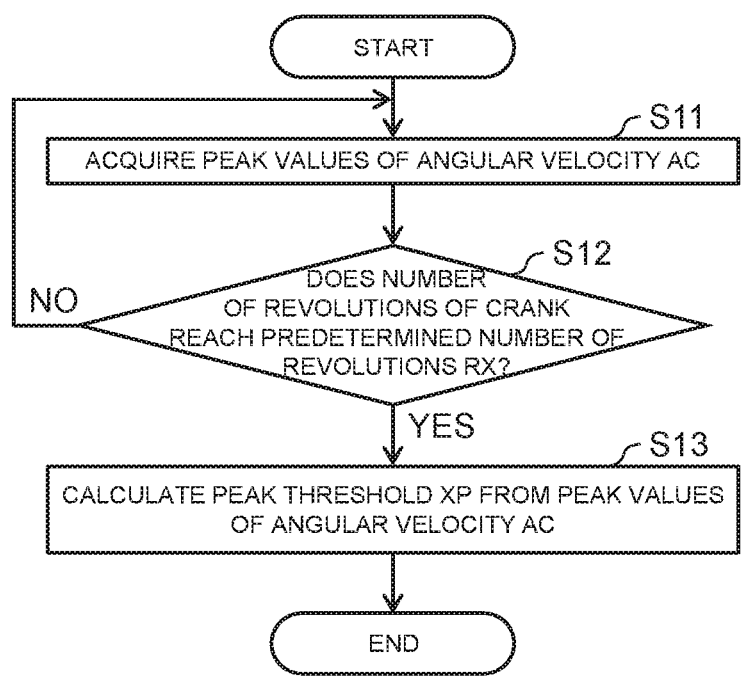
FIG. 13 is a flowchart of a first process executed by the control section.

FIG. 13 illustrates steps of the first process. Control section 21 acquires a peak of angular velocity AC at step S11. The peak of angular velocity AC is stored in storage section 24. Control section 21 determines at step S12 whether the number of revolutions of crank 32 reaches the predetermined number of revolutions RX. When determining that the number of revolutions of crank 32 does not yet reach the predetermined number of revolutions RX, control section 21 returns this process to step S11. When determining that the number of revolutions of crank 32 reaches the predetermined number of revolutions RX, control section 21 calculates peak threshold XP from the plurality of peaks of angular velocity AC at step S13, and terminates the first process. In this process, after acquiring peaks of angular velocity AC when the number of revolutions of crank 32 reaches the predetermined number of revolutions RX, control section 21 calculates peak threshold XP.

Figure 14:
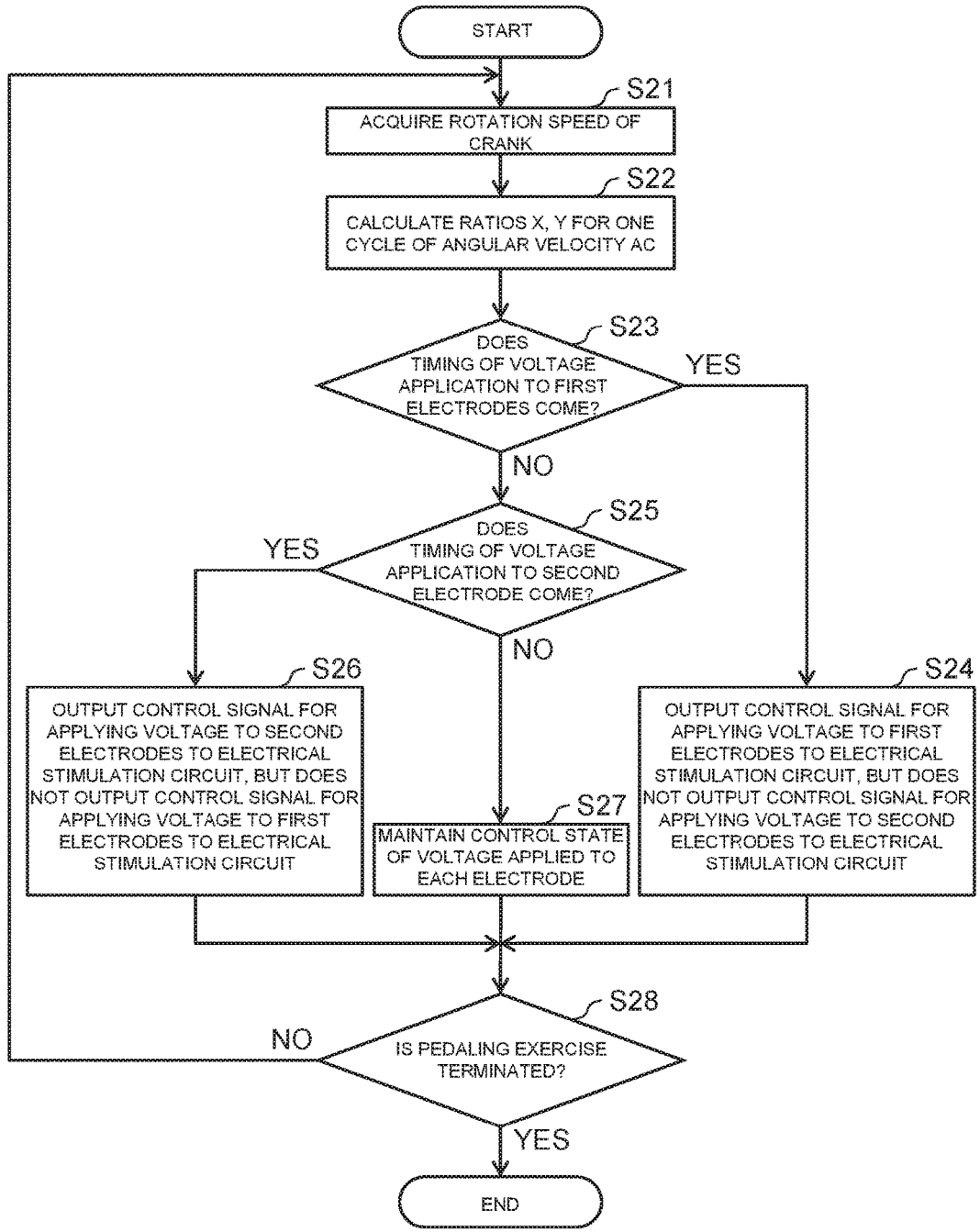
FIG. 14 is a flowchart of a second process executed by the control section.

FIG. 14 illustrates steps of the second process. The second process for a right lower limb will be described with reference to FIG. 14. Note that the similar steps are applied to the second process for a left lower limb.

Control section 21 acquires a rotation speed of crank 32 at step S21. At step S22, control section 21 calculates ratios X, Y from the rotation speed of crank 32, using maps MPX, MPY. Accordingly, timings at which voltages are applied to respective electrodes 12, 13 are set. Control section 21 determines at step S23 whether the timing at which the voltage is applied to first electrodes 12 comes. When determining that the timing at which the voltage is applied to first electrodes 12 comes, the control section 21 outputs a control signal for applying the voltage to first electrodes 12 to electrical stimulation circuit 27 at step S24. However, the control section 21 does not output a control signal for applying the voltage to second electrodes 13 to electrical stimulation circuit 27. As a result, first electrodes 12 start giving electrical stimulation to the quadriceps femoris. When the number of revolutions of crank 32 is RX+1, second electrodes 13 do not start giving electrical stimulation to the biceps femoris. When the number of revolutions of crank 32 exceeds RX+2, namely, after the voltage is started being applied to second electrodes 13, second electrodes 13 stops giving electrical stimulation to the biceps femoris.

When determining that the timing at which a voltage is applied to first electrodes 12 does not yet come, control section 21 determines at step S25 whether the timing at which the voltage is applied to second electrodes 13 comes. When determining that the timing at which the voltage is applied to second electrodes 13 comes, at step S26 control section 21 outputs the control signal for applying the voltage to second electrodes 13 to electrical stimulation circuit 27. However, the control section 21 does not output the control signal for applying the voltage to first electrodes 12 to electrical stimulation circuit 27. As a result, second electrodes 13 starts giving electrical stimulation to the biceps femoris, whereas first electrodes 12 stop giving electrical stimulation to the quadriceps femoris.

When determining at step S25 that the timing at which the voltage is applied to second electrodes 13 does not yet come, at step S27 control section 21 maintains a control state of the voltages to first and second electrodes 12, 13.

Control section 21 determines at step S28 whether the pedaling exercise is terminated. Control section 21 makes the determination at step S28, based on the period of the pedaling exercise which has been set by operation section 25. When determining that the pedaling exercise is not terminated, the control section 21 returns this process return to step S21. When determining that the pedaling exercise is terminated, the control section 21 terminates the second process.

Figure 15:
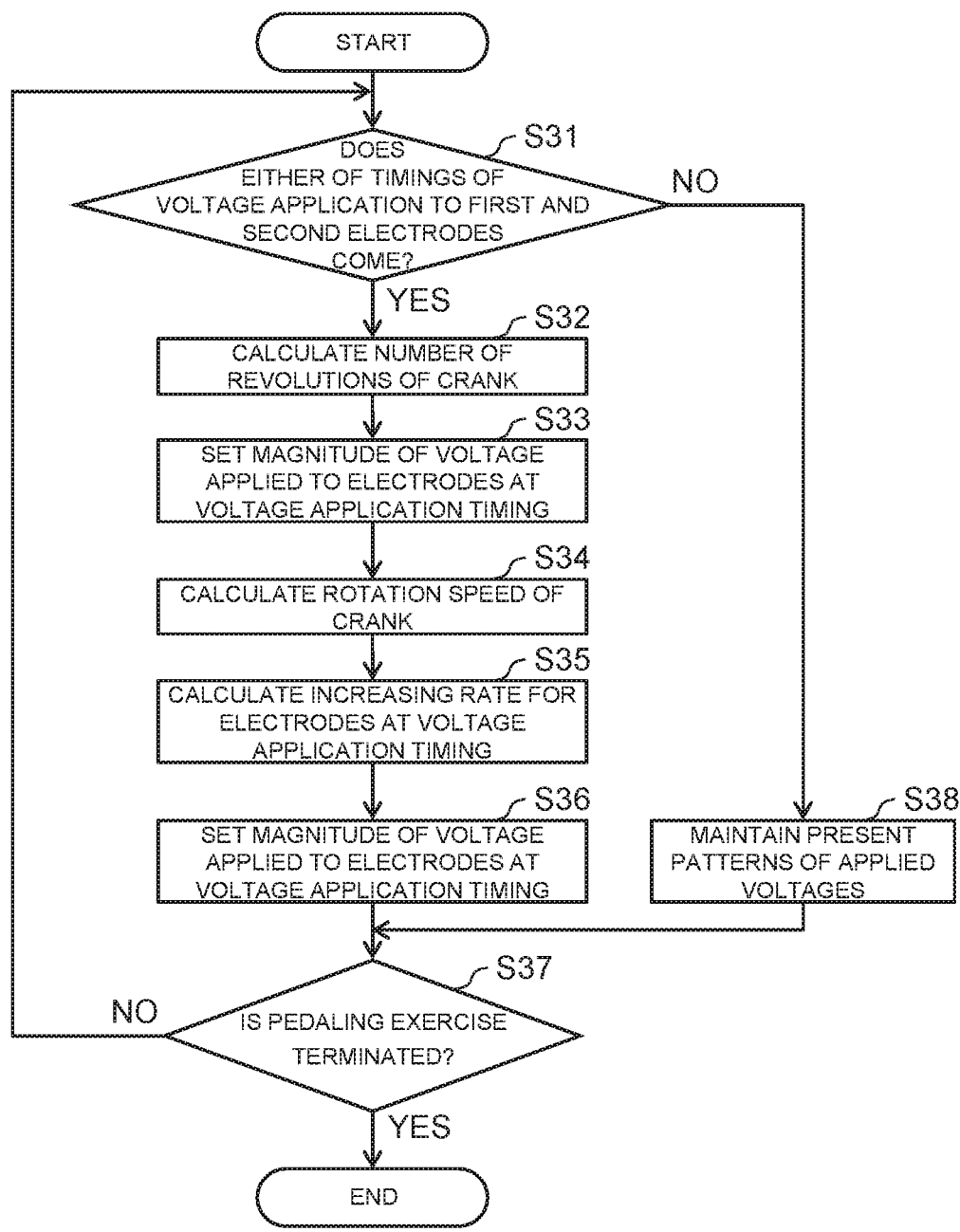
FIG. 15 is a flowchart of a third process executed by the control section.

FIG. 15 illustrates steps of the third process. Control section 21 determines at step S31 whether either of the timings at which the voltages are applied to electrodes 12, 13 comes. When determining that either of the timings at which the voltages are applied to respective electrodes 12, 13 comes, at step S32 control section 21 calculates the number of revolutions of crank 32 at this time. At step S33, control section 21 sets magnitude of a voltage applied to first electrodes 12 or second electrodes 13, whose voltage application timing comes, based on the number of revolutions of crank 32.

At step S34, control section 21 calculates a rotation speed of crank 32. At step S35, control section 21 calculates an increasing rate of the voltage applied to ones of first electrodes 12 or second electrodes 13, whose voltage application timing comes, based on the rotation speed of crank 32. At step S36, control section 21 sets magnitude of the voltage applied to first electrodes 12 or second electrodes 13, whose voltage application timing comes, based on the increasing rate calculated at step S35.

Control section 21 determines at step S37 whether the pedaling exercise is terminated. When determining that the pedaling exercise is not terminated, control section 21 returns this process to S31. When determining that the pedaling exercise is terminated, control section 21 terminates the third process.

When determining at step S31 that neither of the timings at which the voltage is applied to first electrodes 12 and at which the voltage is applied to second electrodes 13 comes, control section 21 maintains the present patterns of the voltages applied to respective electrodes 12, 13 at step S38 so as to proceed to the determination at step S37.

Second Exemplary Embodiment

Electrical stimulation apparatus 100 according to the second exemplary embodiment differs from electrical stimulation apparatus 10 according to the first exemplary embodiment in setting reference points of ratio X of a first phase difference and ratio Y of a second phase difference. In other respects, electrical stimulation apparatus 100 according to the second exemplary embodiment employs a substantially same configuration as the configuration of electrical stimulation apparatus 10 according to the first exemplary embodiment. Here, the components common to the components of electrical stimulation apparatus 10 according to the first exemplary embodiment will be assigned the same reference numerals to describe electrical stimulation apparatus 100 according to the second exemplary embodiment. Description of the common components will be partially or entirely omitted.

Electrical stimulation apparatus 100 according to the present exemplary embodiment will be described below, focusing on the difference from the first exemplary embodiment.

As illustrated in FIG. 3, electrical stimulation apparatus 10 according to the first exemplary embodiment sets reference point Z1 of the ratio (ratio X) of the first phase difference and the ratio (ratio Y) of the second phase difference to a peak of line L1. Electrical stimulation apparatus 100 according to the present exemplary embodiment sets reference point Z2 of the ratio (ratio X) of the first phase difference and the ratio (ratio Y) of the second phase difference to a point different from peak Z1 of line L1.

A method for setting reference point Z2 of the ratio (ratio X) of the first phase difference and the ratio (ratio Y) of the second phase difference according to the present exemplary embodiment will be described below.

Figure 16:
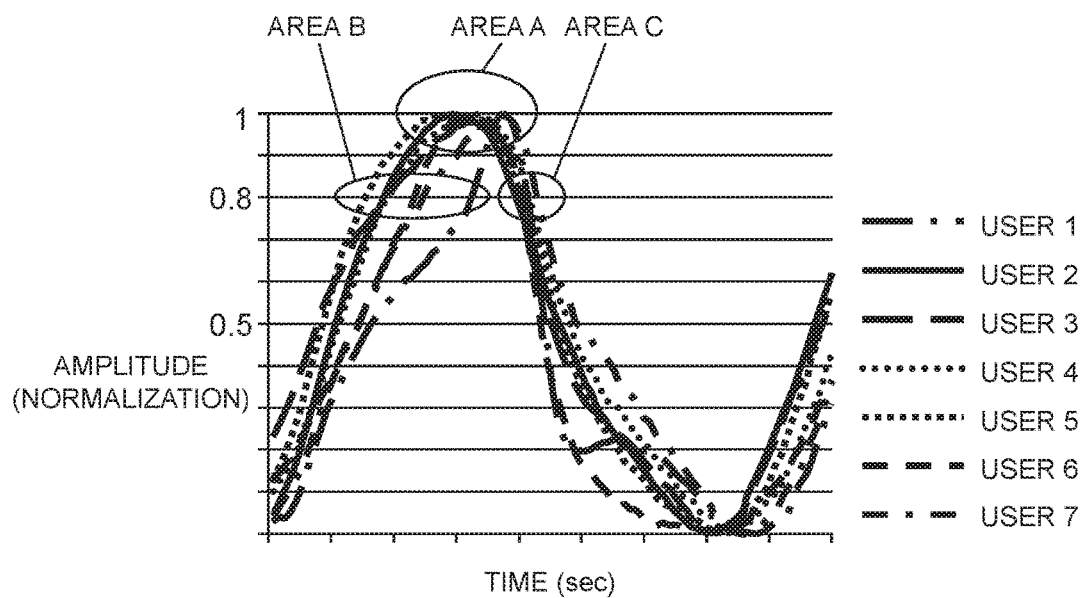
FIG. 16 is a graph illustrating a change in one cycle of an angular velocity of seven users when the crank rotates forward.

FIG. 16 illustrates a change in one cycle of an angular velocity of users 1 to 7 (seven people) when crank 32 rotates forward. A vertical axis indicates a normalized amplitude, and a horizontal axis indicates a lapse of time. As illustrated in FIG. 16, near a peak of an angular velocity waveform (area A) and before a peak (area B), the angular velocity waveform significantly varies between the users. When angular velocities corresponding to area A and area B in which the angular velocity waveform significantly varies are set to reference point Z2 of the ratio (ratio X) of the first phase difference and the ratio (ratio Y) of the second phase difference, adjustment accuracy of an electrical stimulation output timing is likely to deteriorate.

In area C which is an area in which the angular velocity waveform lowers from a peak to a bottom, the angular velocity waveform varies little between the users. When angular velocities corresponding to area C in which the angular velocity waveform varies little are set to reference point Z2 of the ratio (ratio X) of the first phase difference and the ratio (ratio Y) of the second phase difference, adjustment accuracy of an electrical stimulation output timing improves.

In this regard, control section 21 stores in advance a reference point determination condition (e.g., an angular velocity corresponding to 0.8 of a normalized amplitude) of the reference point of the ratio (ratio X) of the first phase difference and the ratio (ratio Y) of the second phase difference. Further, control section 21 determines whether or not a value of the measured angular velocity satisfies the reference point determination condition during pedaling exercise, and determines a point that satisfies the determination condition as the reference point. In this regard, the reference point determination condition stored in advance in control section 21 is determined according to the following method, for example. The degree of variation of the angular velocity waveform in each area is measured by using a standard deviation of a value of a time of each user corresponding to a predetermined amplitude. Further, the angular velocity of an area of a small degree of variation of the angular velocity waveform is determined according to the determination condition of reference point Z2 of the ratio (ratio X) of the first phase difference and the ratio (ratio Y) of the second phase difference.

Figure 17:
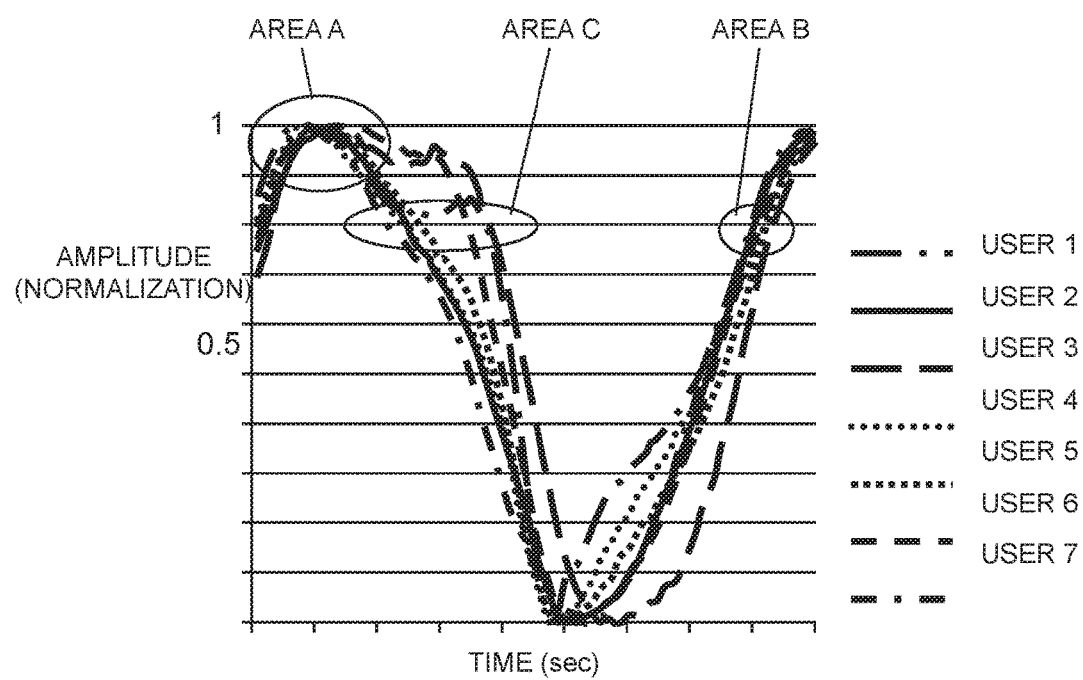
FIG. 17 is a graph illustrating a change in one cycle of an angular velocity of seven users when the crank rotates backward.

FIG. 17 illustrates a change in one cycle of an angular velocity of users 1 to 7 (seven people) when crank 32 rotates backward. A vertical axis indicates a normalized amplitude, and a horizontal axis indicates a lapse of time. As illustrated in FIG. 17, near a peak of an angular velocity waveform (area A) and after a peak (area C), the angular velocity waveform significantly varies between the users. By contrast with this, before the peak (area B), the angular velocity waveform varies little between the users. Hence, during backward rotation of crank 32, the angular velocity corresponding to area B may be set to reference point Z3 of the ratio (ratio X) of the first phase difference and the ratio (ratio Y) of the second phase difference. Thus, control section 21 may change the reference point according to a rotation direction of crank 32.

In this regard, as illustrated in FIGS. 16 and 17, in an area that is shifted by a predetermined value from the peak and the bottom of the angular velocity waveform, the angular velocity waveform varies little between the users. This is a case where a joint angle of a lower limb is a maximum stretch or a maximum bend, and relates to a small degree of variation.

As described above, the reference point determination condition is determined based on the variation of the change in the angular velocity between a plurality of users. However, the present disclosure is not limited to this. The reference point determination condition can be determined based on the variation of the change in the angular velocity according to a pedal type and a displacement condition. That is, control section 21 stores the reference point determination condition set based on the variation of a plurality of items of angular velocity data acquired in advance.

Third Exemplary Embodiment

Electrical stimulation apparatus 1000 according to the third exemplary embodiment differs from electrical stimulation apparatus 10 according to the first exemplary embodiment in applying a voltage to each of electrodes 12, 13 during a period in which a number of revolutions of crank 32 is equal to or less than a predetermined number of revolutions RX. In other respects, electrical stimulation apparatus 1000 according to the third exemplary embodiment includes a substantially same configuration as the configuration of electrical stimulation apparatus 10 according to the first exemplary embodiment. Here, components common to components of electrical stimulation apparatus 10 according to the first exemplary embodiment will be assigned the same reference numerals to describe electrical stimulation apparatus 1000 according to the third exemplary embodiment, and description of the common components will be partially or entirely omitted.

Electrical stimulation apparatus 1000 according to the present exemplary embodiment will be described below, focusing on the difference from the first exemplary embodiment.

As described above, electrical stimulation apparatus 10 according to the first exemplary embodiment does not apply the voltage to each of electrodes 12, 13 during a first period in which the number of revolutions of crank 32 is equal to or less than the predetermined number of revolutions RX. In this case, a user does not feel electrical stimulation while doing pedaling exercise. This may cause the user discomfort.

Figure 18:
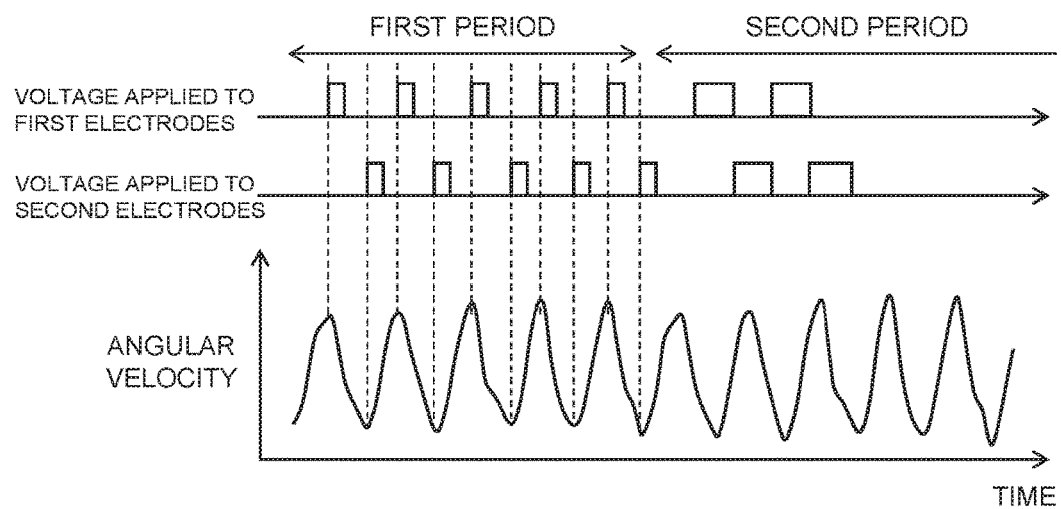
FIG. 18 is a graph illustrating the voltages applied to the respective electrodes.
Figure 19:
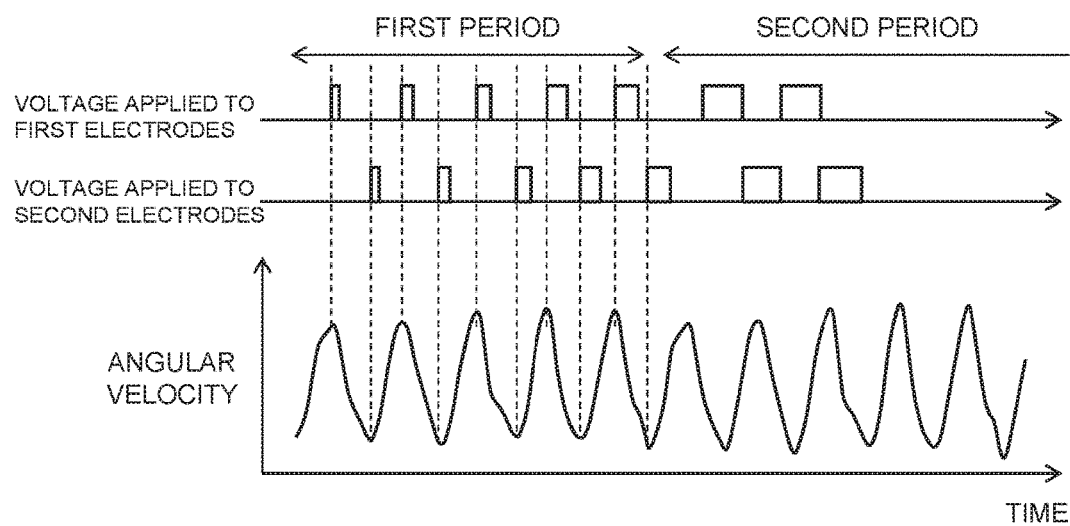
FIG. 19 is a graph illustrating the voltages applied to the respective electrodes.

As illustrated in FIGS. 18 and 19, in electrical stimulation apparatus 1000 according to the present exemplary embodiment, control section 21 executes first control of applying the voltage to each of electrodes 12, 13 even during the first period in which the number of revolutions of crank 32 is equal to or less than the predetermined number of revolutions RX (five rotations in the present exemplary embodiment). Consequently, it is possible to reduce user discomfort. In this regard, control executed by control section 21 to set a timing of voltage application to each of electrodes 12, 13 by reflecting a degree of phase delay of angular velocity AC due to a rotation speed of crank 32 described in the first exemplary embodiment will be referred to as second control.

As described below, according to the first control, the voltage is applied to each of electrodes 12, 13 at a timing different from the timing of voltage application to each of electrodes 12, 13 (second control) that reflects the degree of phase delay of angular velocity AC due to the rotation speed of crank 32.

A description will now be given of the timing of voltage application to each of electrodes 12, 13, a magnitude of an applied voltage, and an application period when the number of revolutions of crank 32 is equal to or less than the predetermined number of revolutions RX (the five rotations in the present exemplary embodiment).

<Application Timing>

As illustrated in FIGS. 18 and 19, in the present exemplary embodiment, when angular velocity detector 14 detects a peak value of an angular velocity, the voltage is applied to first electrode 12. When angular velocity detector 14 detects a bottom value of the angular velocity, the voltage is applied to second electrode 13. The present disclosure is not limited to this, and an application timing can be freely set.

<Magnitude of Applied Voltage>

The magnitude of the applied voltage may gradually increase as the number of revolutions of crank 32 increases or may be fixed. Further, the magnitude of the applied voltage may gradually increase in a first half period of the application period and may be fixed after the first half period of the application period passes.

<Application Period>

The application period may extend as the number of revolutions of crank 32 increases as illustrated in FIG. 19 or may be fixed irrespectively of the number of revolutions of crank 32 as illustrated in FIG. 18.

Further, as illustrated in FIGS. 18 and 19, electrical stimulation apparatus 1000 according to the present exemplary embodiment adjusts an output timing of electrical stimulation according to the degree of phase delay of angular velocity AC and electrically stimulates a predetermined part, as described in the first exemplary embodiment during the second period in which the number of revolutions of crank 32 is larger than the predetermined number of revolutions RX (the five rotations in the present exemplary embodiment).

Modification

The foregoing exemplary embodiment has provided examples of embodiments of a control device for an electrical stimulation apparatus, an electrical stimulation apparatus, and a pedaling exercise system in the present disclosure, and therefore is not intended to limit the present disclosure. A control device for an electrical stimulation apparatus, an electrical stimulation apparatus, and a pedaling exercise system in the present disclosure may employ embodiments of some modifications of the foregoing exemplary embodiment which will be described below or combinations of two or more of these modifications which are not mutually contradictory.

In the foregoing exemplary embodiment, control section 21 may calculate the number of revolutions and rotation speed of crank 32, based on a detection signal from a crank sensor. Moreover, control section 21 may set voltages applied to respective electrodes 12, 13, based on the detection signal from the crank sensor.

In the foregoing exemplary embodiment, control section 21 may be provided inside pedaling exercise machine 30. In this case, pedaling exercise machine 30 is electrically connected to first electrodes 12, second electrodes 13, and angular velocity detectors 14 in supporters 11. Furthermore, controller 20 and pedaling exercise machine 30 may be integrated with each other.

In the foregoing exemplary embodiment, only one angular velocity detector 14 may be provided in either of supporters 11.

In the foregoing exemplary embodiment, state detector 22 may include a bottom detector that detects a bottom of a detection signal from each angular velocity detector 14. Control section 21 may calculate an amplitude of angular velocity AC from the peak and bottom of angular velocity AC.

In the foregoing modification, voltage-application timing setting section 23A may set the timings at which the voltages are applied to respective electrodes 12, 13 based on ratios X, Y preset for the amplitude of angular velocity AC.

In the foregoing modification, when the bottom detector is provided to state detector 22, peak detector 22C do not necessarily have to be provided to state detector 22. In this case, control section 21 calculates one cycle of angular velocity AC, and the number of revolutions and rotation speed of crank 32, based on the bottom detected by the bottom detector.

In the foregoing exemplary embodiment, control section 21 may calculate one cycle of angular velocity AC, based on zero crossing points of angular velocity AC, instead of based on neighboring peaks of angular velocity AC.

In the foregoing exemplary embodiment, filter switch 22F may further include a third filter whose frequency response differs from frequency response of the first filter and the second filter. In this case, filter switch 22F may switch between filters, at least once, to smooth an angular velocity detected by angular velocity detector 14 over the period between the start and the termination of the pedaling exercise done by a user.

In the foregoing exemplary embodiment, control section 21 may compensate for the increasing rates of the voltages applied to respective electrodes 12, 13 which are related to an increase in the number of revolutions of crank 32, based on a rotation speed of crank 32. Applied-voltage setting section 23B makes this compensation so that the increasing rates of the voltages applied to respective electrodes 12, 13 increase with an increase in the rotation speed of crank 32. With this compensation, when crank 32 rotates at a high speed, voltages applied to respective electrodes 12, 13 at a small number of revolutions of crank 32 are set as their set voltages.

In the foregoing exemplary embodiment, applied-voltage setting section 23B may set the maximum values of voltages applied to respective electrodes 12, 13 in a variable manner, in accordance with the number of revolutions of crank 32. For example, after the set voltages have been applied to respective electrodes 12, 13, applied-voltage setting section 23B may gradually decrease the maximum values of the voltages applied to respective electrodes 12, 13 from the set voltages according as the number of revolutions of crank 32 increases. Alternatively, applied-voltage setting section 23B may vary the maximum values of the voltages applied to respective electrodes 12, 13, in accordance with the number of revolutions of the crank 32.

In the foregoing exemplary embodiment, a user may do the pedaling exercise with both arms. In this case, supporters 11 are attached to the right and left upper arms respectively. In this case, first electrodes 12 is disposed at a location related to the biceps brachii muscles, for example, whereas second electrodes 13 is disposed at a location related to the triceps brachii muscles, for example. In addition, angular velocity detector 14 is disposed at a location related to the biceps brachii muscles, for example.

The electrical stimulation apparatus and the pedaling exercise system of the present disclosure may be applied to any electrical stimulation apparatus and any pedaling exercise system for household use, professional use, or any other uses.

What is claimed is:

1. An electrical stimulation apparatus comprising:
a control section;
an electrode; and
an angular velocity detector, wherein the electrode is configured to provide electrical stimulation to a predetermined part of a body doing a pedaling exercise, the exercise being performed by rotating a crank, the predetermined part being at least one of a leg and an arm, the angular velocity detector is configured to be disposed on the predetermined part and configured to detect an angular velocity of the predetermined part, the angular velocity being a result of an operation of the predetermined part during the pedaling exercise, the control section is configured to:
  communicate with the angular velocity detector,
  adjust, according to a result of the detection in the angular velocity detector, an output timing of the electrical stimulation of the electrode such that the electrode provides electrical stimulation to the predetermined part when a state of the operation of the predetermined part during the pedaling exercise is a predetermined operation state, and
  adjust an output timing of a current of the electrode according to the result of the detection in the angular velocity detector and a phase delay of the result of the detection in the angular velocity detector in response to the angular velocity of the predetermined part.

2. The apparatus of claim 1, wherein the control section is further configured to adjust the output timing based on a rotation speed of the crank.

3. The apparatus of claim 1, wherein the control section is configured to smooth the result of the detection in the angular velocity detector by using a first filter when a number of revolutions of the crank during the pedaling exercise is included in a first range, and to smooth the result of the detection in the angular velocity detector by using a second filter having a frequency response curve with a slope smaller than that of the first filter when a number of revolutions of the crank during the pedaling exercise is included in a second range higher than the first range.

4. The apparatus of claim 1, wherein the control section is further configured to detect, based on a representative value of a peak or a bottom of an angular velocity during a first period, a peak or a bottom of an angular velocity during a second period, the first period being a period in which a number of revolutions of the crank during the pedaling exercise is equal to or less than a predetermined number of revolutions, and the second period being a period after the number of revolutions of the crank exceeds the predetermined number of revolutions.

5. The apparatus of claim 1, wherein the control section is further configured to determine the output timing of the electrical stimulation based on a predetermined reference point, and to determine the predetermined reference point based on a reference point determination condition set based on a variation of a plurality of items of angular velocity data acquired in advance of the exercise being performed.

6. The apparatus of claim 1, wherein the control section is configured to execute control to electrically stimulate the predetermined part at a timing during a first period, the timing being different from the output timing of the electrical stimulation adjusted by the control section, and the first period being a period in which a number of revolutions of the crank during the pedaling exercise is equal to or less than a predetermined number of revolutions.

7. The apparatus of claim 1, wherein the control section is configured to execute control not to electrically stimulate the predetermined part during a first period being a period in which a number of revolutions of the crank during the pedaling exercise is equal to or less than a predetermined number of revolutions.

8. A pedaling exercise system comprising:
  the electrical stimulation apparatus according to claim 1; and
  a pedal exercise machine.

* * * * *